US012599545B2

(12) United States Patent
Kato et al.

(10) Patent No.: US 12,599,545 B2
(45) Date of Patent: Apr. 14, 2026

(54) DENTAL ADHESIVE COMPOSITION, DENTAL ADHESIVE MATERIAL, AND DENTAL ADHESIVE MATERIAL PACKAGE

(71) Applicant: Tokuyama Dental Corporation, Tokyo (JP)

(72) Inventors: Akane Kato, Tokyo (JP); Keishi Fukudome, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 943 days.

(21) Appl. No.: 17/756,959

(22) PCT Filed: Oct. 29, 2020

(86) PCT No.: PCT/JP2020/040700
§ 371 (c)(1),
(2) Date: Jun. 6, 2022

(87) PCT Pub. No.: WO2021/111782
PCT Pub. Date: Jun. 10, 2021

(65) Prior Publication Data

US 2023/0022464 A1 Jan. 26, 2023

(30) Foreign Application Priority Data

Dec. 5, 2019 (JP) ................................ 2019-220655
Feb. 19, 2020 (JP) ................................ 2020-026222

(51) Int. Cl.
*A61K 6/30* (2020.01)
*A61K 6/60* (2020.01)
*A61K 6/76* (2020.01)

(52) U.S. Cl.
CPC .................. *A61K 6/30* (2020.01); *A61K 6/60* (2020.01); *A61K 6/76* (2020.01)

(58) Field of Classification Search
CPC ........................................................ A61K 6/30
See application file for complete search history.

(56) References Cited

U.S. PATENT DOCUMENTS 9,974,716 B2 * 5/2018 Catel ........................ A61K 6/60
2016/0022549 A1 1/2016 Catel et al.

FOREIGN PATENT DOCUMENTS

EP 0237233 A2 * 9/1987 ............... A61K 6/62
JP 2003-230574 A 8/2003
JP 2006-225350 A 8/2006
JP 2007-277114 A 10/2007
JP 2016-513627 A 5/2016
JP 2019-64937 A 4/2019
JP 2019-151595 A 9/2019
WO 2019/172132 A1 9/2019

OTHER PUBLICATIONS

International Search Report dated Dec. 28, 2020 in International Application No. PCT/JP2020/040700.
Supplementary European Search Report dated Jan. 2, 2024 in European Application No. 20896983.2.

* cited by examiner

*Primary Examiner* — Brieann R Johnston
(74) *Attorney, Agent, or Firm* — SALIWANCHIK, LLOYD & EISENSCHENK

(57) ABSTRACT

[Object] To provide a dental adhesive composition that is highly adhesive to both porcelain and a tooth substance, an acid monomer, water, and a silane coupling agent coexisting in the dental adhesive composition, the dental adhesive composition being usable as a one-liquid type adhesive and exhibiting high preservation stability as a one-liquid type adhesive even after long-term preservation, regardless of the type of acid monomer used.
[Solving Means] There is provided a dental adhesive composition characterized by including a mixture that includes a silane coupling agent (A) that does not have a silyl ether structure and includes an organic silane compound (a1) in which four monovalent groups are bonded to one silicon atom, the four monovalent groups including (i) a monovalent group having a radical polymerizable group and (ii) a monovalent group that has an alkylene chain having 3 to 40 carbon atoms and an unsaturated bond in a carbon atom at a β-position from the silicon atom; a fluoride salt (B); a polymerizable monomer (C) that contains an acidic group-containing polymerizable monomer (c1); water (D); and an organic solvent (E).

6 Claims, No Drawings

DENTAL ADHESIVE COMPOSITION, DENTAL ADHESIVE MATERIAL, AND DENTAL ADHESIVE MATERIAL PACKAGE

CROSS-REFERENCE TO RELATED APPLICATIONS

This application is the U.S. national stage application of International Patent Application No. PCT/JP2020/040700, filed Oct. 29, 2020, which claims the benefit under 35 U.S.C. § 119 of Japanese Application Nos. 2019-220655, filed Dec. 5, 2019; and 2020-026222, filed Feb. 19, 2020; the disclosures of each of which are incorporated herein by reference in their entirety.

TECHNICAL FIELD

The present invention relates to a novel dental composition. Specifically, the present invention relates to a novel dental composition containing an organic silane compound having a specific structure, a fluoride salt, an acidic compound, water, and an organic solvent.

BACKGROUND ART

In dental treatment, when filling a cavity from which dental caries were removed with a restoration material, it is necessary to adhere various materials to a tooth substance. There are various types of restoration materials such as a composite resin, a metal, zirconia, alumina, lithium disilicate glass, and porcelain. In the past, in order to bond the tooth substance or the restoration material, it has been necessary to use an adhesive material dedicated to each material and the operation has been complicated. In this regard, in order to simplify the operation, an adhesive material having adhesiveness to both a tooth substance and a restoration material by adding an adhesive component to a tooth substance and an adhesive component to various restoration materials to one composition has been proposed.

In such a dental adhesive material, in order to achieve adhesiveness to a tooth substance, an acidic group-containing polymerizable monomer (hereinafter, referred to also as the "acid monomer") and water are generally formulated as essential components, and a silane coupling agent is generally formulated in order to enhance the adhesiveness to an adherend in the case of using silica ceramics as an adherend. Here, the silane coupling agent means an organosilicon compound or an agent containing the compound as a main component, which has, in the molecule, both a functional group that reacts and bonds with an organic material and a functional group that reacts and bonds with an inorganic material. As the organosilicon compound, an alkoxysilane compound having an alkoxy group that reacts with a silanol group (hydroxy group bonded to a Si atom) present on the surface of an inorganic material to form a siloxane bond is widely used.

Incidentally, in the case where an acid component, water, and a silane coupling agent coexist, the silane coupling agent is hydrolyzed and condensed to from an oligomer and is inactivated. For this reason, in a dental adhesive material containing these components, generally, they are preserved separately in a plurality of (usually two) agents so that they do not coexist and both agents are mixed and used at the time of use (see Patent Literatures 1 and 2). In such a so-called two-liquid type dental adhesive material, it is necessary to weigh and mix both the agents so that an appropriate formulation ratio can be achieved at the time of use.

Meanwhile, several one-liquid type adhesive materials that do not require an operation of weighing and mixing the respective agents and have improved operations have been proposed. For example, Patent Literature 3 discloses "an adhesive composition for dental restorations formed of ceramics in a preservation form in which respective components of (A) a radical polymerizable monomer; (B) a silane coupling agent; (C) a sensitive dye; (D) a photoacid generating agent and/or a photobase generating agent; and (E) a photoradical generating agent, or an aryl borate compound or sulfinate in the case where a photoacid generating agent was used as the (D) component are mixed into one agent. Then, in accordance with the technology described in Patent Literature 3, it is possible to provide an adhesive composition capable omitting the operation of mixing reagents immediately before use because the adhesive composition has high adhesiveness such that prior primer treatment can be omitted and can be stably preserved for a long period of time in the state where the respective components constituting the adhesive composition are mixed in one agent.

Further, Patent Literature 4 proposes a curable composition for medical and dental use characterized by including (1) an organic silane compound characterized by having at least one radical polymerizable group, an alkylene chain that may have a linear or branched $C_3$ to $C_{40}$ phenyl group to be bonded to a silicon atom having an unsaturated bond at a β-position carbon from the silicon atom, (2) a phosphonic acid group-containing polymerizable monomer, (3) a multivalent carboxylic acid group-containing polymerizable monomer, (4) a polymerizable monomer, (5) water, (6) a water-soluble organic solvent, and (7) a polymerization initiator. Then, Patent Literature 4 shows that the preservation stability and durability of the curable composition for medical and dental use are both favorable. Further, Patent Literature 4 describes that the reason why such an effect can be achieved is presumably that the reaction mechanism when the (1) organosilicon compound is bonded to an adherend formed of an inorganic material, e.g., in the case of an organic silane compound to which an allyl group is bonded, the reaction mechanism in which hydrogen is taken away from a silanol group present on the surface of the adherend and the generated oxygen anion attacks a silicon atom of the organic silane compound (with desorption of propene) to form a covalent bond, is less likely to deteriorate or change in nature due to hydrolysis because the reaction mechanism is different from the existing reaction mechanism of a bond a silane coupling agent having an alkoxy group.

CITATION LIST

Patent Literature

Patent Literature 1: Japanese Patent Application Laid-open No. 2003-230574

Patent Literature 2: Japanese Patent Application Laid-open No. 2006-225350

Patent Literature 3: Japanese Patent Application Laid-open No. 2007-277114

Patent Literature 4: Japanese Patent Application Laid-open No. 2019-64937

DISCLOSURE OF INVENTION

Technical Problem

The composition including a silane coupling agent and a photoacid generating agent illustrated in Patent Literature 3 is capable of enhancing the preservation stability by not allowing the silane coupling agent to coexist with an acid or a base that is a catalyst necessary for hydrolysis/condensation reaction of the silane coupling agent during preservation, but it is necessary to use, as the catalyst, a photoacid generating agent and/or a photobase generating agent that functions only when light is applied thereto and also the polymerization curing method is limited to the photopolymerization method. Further, since an acid monomer is not used, the adhesiveness to a tooth substance tends to be lower than that of a system containing an acid monomer.

Meanwhile, since the (1) organic silane compound described in Patent Literature 4 is an organosilicon compound that has, in the molecule, both a functional group that reacts and bonds with an organic material and a functional group that reacts and bonds with an inorganic material, it can be said to be a silane coupling agent in a broad sense. However, it is a silane coupling agent (hereinafter, a silane coupling agent that reacts and bonds with an inorganic material by a mechanism similar to that of the silicon compound described in Patent Literature 4 will be referred to as the "hydrolysis-resistant silane coupling agent") including an organosilicon compound that has no hydrolysable group such as an alkoxy group, unlike the existing general silane coupling agent having hydrolyzability, such as alkoxysilane (hereinafter, referred to also as the "hydrolysable silane coupling agent"). Then, also the reaction mechanism for being bonded to an inorganic material is different from "hydrolysis of a hydrolysable group such as an alkoxy group and formation of a siloxane bond by dehydration condensation of a silanol group generated by the hydrolysis and a silanol group on the surface of an inorganic material" in the existing general hydrolysable silane coupling agent as described above. For this reason, The curable composition for medical and dental use using a hydrolysis-resistant silane coupling agent described in Patent Literature 4 has advantages that high preservation stability is achieved with one-liquid type, the polymerization form is not particularly limited, and the adhesiveness to a tooth substance is high because it contains an acid monomer.

However, in the curable composition for medical and dental use, the (2) phosphonic acid group-containing polymerizable monomer and the (3) multivalent carboxylic acid group-containing polymerizable monomer are combined with each other an acid monomer, and the effects described have not been verified for a composition in which both of them are not combined with each other. In this regard, when the present inventors evaluated the performance of a composition including, as an acid monomer, the organosilicon compound and water by the composition in which the (2) phosphonic acid group-containing polymerizable monomer and the (3) multivalent carboxylic acid group-containing polymerizable monomer are not combined with each other, it was confirmed that the adhesive performance after long-term preservation deteriorated in some cases (see Comparative Example 2 and Comparative Examples 6 to 8 described below).

In this regard, it is an object of the present invention to provide a dental adhesive composition that is usable as a one-liquid type adhesive, an acid monomer, water, and a hydrolysis-resistant silane coupling agent coexisting in the dental adhesive composition, the dental adhesive composition being highly adhesive to both silica ceramics and a tooth substance (capable of exhibiting high preservation stability) reliably even after long-term preservation, regardless of the type of acid monomer used.

Solution to Problem

The present inventors made diligent studies to solve the technical problems described above. As a result, they found that when a fluoride salt serving as a fluoride ion source is formulated in a dental adhesive composition that includes a hydrolysis-resistant silane coupling agent, an acid monomer, and water, preservation stability and adhesive durability could be improved with good reproducibility regardless of the type of acid monomer used, and completed the present invention.

That is, the first present invention is a dental adhesive composition characterized by including a mixture that includes a silane coupling agent (A) that does not have a silyl ether structure and includes an organic silane compound (a1) in which four monovalent groups are bonded to one silicon atom, the four monovalent groups including (i) a monovalent group having a radical polymerizable group and (ii) a monovalent group that has an alkylene chain having 3 to 40 carbon atoms and has an unsaturated bond in a carbon atom at a β-position from the silicon atom, a fluoride salt (B), a polymerizable monomer (C) that contains an acidic group-containing polymerizable monomer (c1), water (D), and an organic solvent (E).

In the dental adhesive composition according to the present invention, the (a1) organic silane compound is favorably represented by the following general formula 1, and 0.01 to 10 mol of the fluoride salt (B) with respect to 1 mol of the organic silane compound (a1) is favorably contained.

[Chem. 1]

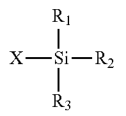
(1)

(In general formula (1),

X represents a monovalent organic group having a radical polymerizable group, $R_1$, $R_2$, and $R_3$ represent monovalent organic groups of the same kind or different kinds, and at least one of $R_1$, $R_2$, and $R_3$ represents a monovalent organic group represented by the following general formula (2).)

[Chem. 2]

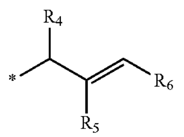
(2)

(In the general formula (2),

* represents a position where the monovalent organic group is bonded to a silicon atom in the general formula 1, and $R_4$, $R_5$, and $R_6$ each represent a hydrogen atom; a phenyl group; an unsubstituted alkyl group having 1 to 20 carbon atoms; a substituted alkyl group having 1 to 20 carbon atoms in which 1 or a plurality of hydrogen atoms are substituted with at least one of an alkoxy group, a siloxy group, and an amino group; or a monovalent organic group having an —O— bond, a —C(=O)—O— bond, or an —NH— bond between a C—C bond of a main chain of the unsubstituted alkyl group or the substituted alkyl group having 2 to 20 carbon atoms.)

The second present invention is a dental adhesive material including the dental adhesive composition according to the present invention. The dental adhesive material according to the present invention is favorably a dental adhesive material for adhering a first adherend that has an adhesive surface formed of an inorganic substance having a silanol group on a surface thereof and a second adherend that includes a curable composition containing a polymerizable monomer or a cured body thereof to each other.

The third present invention is a dental adhesive material package including the dental adhesive composition according to the present invention contained in a single container.

Advantageous Effects of Invention

The dental adhesive composition according to the present invention exhibits not only high adhesive strength and adhesive durability to porcelain in addition to a composite resin and a tooth substance but also high preservation stability even in the case where it is formed as a one-liquid type dental adhesive composition in which these components coexist. However, unlike the existing one-liquid type dental adhesive composition, it is unnecessary to use a photoacid generating agent and the effects described above can be exhibited regardless of the type of acid monomer used.

MODE(S) FOR CARRYING OUT THE INVENTION

The dental adhesive composition according to the present invention inhibits the activity (as a coupling agent) from decreasing due to hydrolysis/condensation during preservation, which is unavoidable in the case where the existing general silane coupling agent having a hydrolysable group such as an alkoxy group coexists with an acid and water, by using a hydrolysis-resistant silane coupling agent, i.e., "an organic silane compound having at least one radical polymerizable group, an alkylene chain that may have a linear or branched $C_3$ to $C_{40}$ phenyl group to be bonded to a silicon atom having an unsaturated bond at a β-position carbon from the silicon atom" similarly to the curable composition for medical and dental use described in Patent Literature 4. Then, by further containing the (B) fluoride salt, a high adhesive effect can be exhibited regardless of the type of acid monomer used.

Although the reason why such an effect can be obtained by the coexistence of a fluoride salt is not necessarily clear, this is presumably because since a fluoride ion has a high affinity for a silicon atom, a fluoride ion in the dental adhesive composition according to the present invention causes some interaction with the silicon compound to make the activity higher or a silanol group present on the surface of an adherend interacts with a fluoride ion at the time of application to facilitate the reaction with the silicon compound (hydrolysis-resistant silane coupling agent).

Hereinafter, the respective components used in the dental composition according to the present invention will be described.

<Hydrolysis-Resistant Silane Coupling Agent (A); (A) Component>

A hydrolysis-resistant silane coupling agent used as the (A) component in the present invention is not particularly limited as long as it is an organic silane compound that does not have a silyl ether structure and includes an organic silane compound (a1) in which four monovalent groups are bonded to one silicon atom, the four monovalent groups including (i) a monovalent group having a radical polymerizable group and (ii) a monovalent group that has an alkylene chain having 3 to 40 carbon atoms and has an unsaturated bond in a carbon atom at a β-position from the silicon atom. For example, one including a silicon compound as described in the Patent Literature 4 can be used without particular limitation.

From the viewpoint of achieving high reactivity and stable adhesive strength, it is favorable that in the hydrolysis-resistant silane coupling agent, the organic silane compound (a1) is represented by the following general formula (1).

[Chem. 1]

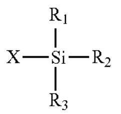

(1)

Note that X in the general formula (1) represents a monovalent organic group having a radical polymerizable group, $R_1$, $R_2$, and $R_3$ represent monovalent organic groups of the same kind or different kinds, and at least one of $R_1$, $R_2$, and $R_3$ represents a monovalent organic group represented by the following general formula (2).

[Chem. 2]

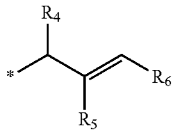

(2)

Note that * in the general formula (2) represents a position where the monovalent organic group represented by the general formula (2) is bonded to a silicon atom in the general formula (1), and $R_4$, $R_5$, and $R_6$ each represent 1) a hydrogen atom; 2) a phenyl group; 3) an unsubstituted alkyl group having 1 to 20 carbon atoms; 4) a substituted alkyl group having 1 to 20 carbon atoms in which 1 or a plurality of hydrogen atoms are substituted with at least one of an alkoxy group, a siloxy group, and an amino group; or 5) a monovalent organic group having an —O— bond, a —C(=O)—O— bond, or an —NH— bond between a C—C bond of a main chain of the unsubstituted alkyl group or the substituted alkyl group having 2 to 20 carbon atoms.

X in the general formula (1) is not particularly limited as long as it is a monovalent organic group that has a radical polymerizable group at one end and is bonded to a silicon atom in the general formula (1) at another end, but the radical polymerizable group is favorably a group having a structure in which the radical polymerizable group and the silicon atom are bonded to each other via a divalent organic group having 1 to 30 carbon atoms in the main chain. Further, in this case, it is favorable that the radical polymerizable group is an acryloxy group, a methacryloxy group, an acrylamide group, or a methacrylamide group and the divalent organic group is an alkylene group or a phenylene group having 1 to 30 carbon atoms, particularly, 1 to 20 carbon atoms in the main chain. Further, all of $R_1$, $R_2$, and $R_3$ in the general formula (1) favorably represent the monovalent organic group represented by the general formula (2). Further, $R_4$ and $R_5$ in the general formula (2) favorably represent a hydrogen atom or a methyl group, and $R_6$ favorably represents a hydrogen atom or an alkyl group having 1 to 3 carbon atoms.

Specific examples of the organic silane compound that can be suitably used as the (A) hydrolysis-resistant silane coupling agent include triallylsilylmethylacrylate, triallylsilylmethylmethacrylate, 2-(triallylsilyl)ethylacrylate, 2-(triallylsilyl)ethylmethacrylate, 3-(triallylsilyl)propylacrylate, 3-(triallylsilyl)propylmethacrylate, 4-(triallylsilyl)butylacrylate, 4-(triallylsilyl)butylmethacrylate, 5-(triallylsilyl)pentylacrylate, 5-(triallylsilyl)pentylmethacrylate, 6-(triallylsilyl)hexylacrylate, 6-(triallylsilyl)hexylmethacrylate, trimethallylsilylmethylacrylate, trimethallylsilylmethylmethacrylate, 2-(trimethallylsilyl)ethylacrylate, 2-(trimethallylsilyl)ethylmethacrylate, 3-(trimethallylsilyl)propylacrylate, 3-(trimethallylsilyl)propylmethacrylate, 4-(trimethallylsilyl)butylacrylate, 4-(trimethallylsilyl)butylmethacrylate, 5-(trimethallylsilyl)pentylacrylate, 5-(trimethallylsilyl)pentylmethacrylate, 6-(trimethallylsilyl)hexylacrylate, 6-(trimethallylsilyl)hexylmethacrylate, 3-(diallylmethylsilyl)propylacrylate, 3-(diallylmethylsilyl)propylmethacrylate, 3-(diallylethylsilyl)propylacrylate, 3-(diallylethylsilyl)propylmethacrylate, 3-(diallylisopropylsilyl)propylacrylate, 3-(diallylisopropylsilyl)propylmethacrylate, 3-(dimethallylmethylsilyl)propylacrylate, 3-(dimethallylmethylsilyl)propylmethacrylate, 3-(dimethallylethylsilyl)propylacrylate, 3-(dimethallylethylsilyl)propylmethacrylate, 3-(dimethallylisopropylsilyl)propylacrylate, 3-(dimethallylisopropylsilyl)propylmethacrylate, 3-(allyldimethylsilyl)propylacrylate, 3-(allyldimethylsilyl)propylmethacrylate, 3-(allyldiethylsilyl)propylacrylate, 3-(allyldiethylsilyl)propylmethacrylate, 3-(allyldiisopropylsilyl)propylacrylate, 3-(allyldiisopropylsilyl)propylmethacrylate, 3-(methallyldimethylsilyl)propylacrylate, 3-(methallyldimethylsilyl)propylmethacrylate, 3-(methallyldiethylsilyl)propylacrylate, 3-(methallyldiethylsilyl)propylmethacrylate, 3-(methallyldiisopropylsilyl)propylacrylate, and 3-(methallyldiisopropylsilyl)propylmethacrylate.

The content of the (A) component in the dental composition according to the present invention is favorably 2 mass parts or more and 50 mass parts or less (hereinafter, "x or more and y or less" will be referred to simply as x to y in some cases), and more favorably 5 to 30 mass parts, when the total amount of the polymerizable monomer that is the (C) component is 100 mass parts, from the viewpoint of the adhesiveness and the preservation stability. As the (A) component, two or more kinds may be combined as necessary.

Note that the (A) component is one of the materials of the mixture forming the dental adhesive composition according to the present invention, but in the case where the (A) component coexists with another component as described above, at least part of the (A) component reacts with or is compounded with another component, whereby there is a possibility that the existence form changes, for example, to a derivative of the (A) component (specifically, a derivative of (a1)). Since it is difficult to specify the form that actually exists in the system, such a form is also treated as the (A) component or (a1) in the present invention.

<Fluoride Salt (B); (B) Component>

The (B) component serves as a fluoride ion source for supplying a fluoride ion to the dental composition according to the present invention, and an inorganic fluoride salt and/or an organic fluoride salt having such a function can be used without particular limitation. Specific examples of the fluoride salt that can be suitably used include lithium fluoride, sodium fluoride, potassium fluoride, rubidium fluoride, magnesium fluoride, calcium fluoride, strontium fluoride, cesium fluoride, aluminum fluoride, ytterbium fluoride, tetramethylammonium fluoride, tetraethylammonium fluoride, tetrabutylammonium fluoride, ammonium fluoride, phosphorylcholine fluoride, and fluoroaluminosilicate. Among these, an organic fluoride salt such as tetramethylammonium fluoride, tetraethylammonium fluoride, tetrabutylammonium fluoride, and phosphorylcholine fluoride are particularly suitably used from the viewpoint of solubility.

From the viewpoint of the effect, the formulation amount of the fluoride salt (B) is favorably an amount that is dissolved in the dental composition according to the present invention, and is favorably 0.01 to 10 mol, particularly 0.05 to 5 mol with respect to 1 mol of the organic silane compound (a1) while satisfying such a condition. When the amount of the (B) component with respect to the (A) component is too small, the adhesion promoting effect is reduced. Further, in the case where the amount of the (B) component is too much, it is overused and inefficient.

Note that the (B) component is one of the materials of the mixture forming the dental adhesive composition according to the present invention, but it is considerable that at least part of the (B) component is dissolved in water and ionized in the mixture and at least part of the ion (fluoride ion) reacts with or is compounded with the (A) component. In this regard, also the (B) component including those in such a state whose form has been changed is treated as the (B) component.

<Polymerizable Monomer (C); (C) Component>

The (C) component needs to contain an acidic group-containing polymerizable monomer (c1). The (C) component may only include the acidic group-containing polymerizable monomer (c1) but favorably includes a polymerizable monomer (c2) having no acidic group because the mechanical strength and water resistance of the adhesive material layer are improved. Hereinafter, these components will be described.

<Acidic Group-Containing Polymerizable Monomer (c1): (c1) Component (Acid Monomer)>

The acidic group-containing polymerizable monomer that is the (c1) component has an effect of decalcifying and plasticizing a tooth substance. Further, an acidic group is chemically bonded to calcium on the surface of the tooth substance to achieve adhesiveness to the tooth substance.

as the (c1) component: acidic group-containing polymerizable monomer (acid monomer) in the (C) component, an acid monomer, used in a general dental adhesive composition, e.g., a compound that has, in the molecule, at least one of a phosphinico group {$=P(=O)OH$}, a phosphono group {$-P(=O)(OH)_2$}, a carboxyl group {$-C(=O)OH$}, a dihydrogen phosphate monoester group {$-O-P(=O)(OH)_2$}, a hydrogen phosphate diester group {$(-O-)_2P(=O)OH$}, a sulfo group ($-SO_3H$), an acid anhydride skeleton {$-C(=O)-O-C(=O)-$}, and the like as an acidic group and has at least one polymerizable unsaturated group can be used without particular limitation.

It is favorable to use an acid monomer having, as an acidic group, a carboxyl group, a dihydrogen phosphate monoester group, or a hydrogen phosphate diester group because stability to water is high, the smear layer on the tooth surface can be gradually dissolved, and tooth can be gradually decalcified. Examples of the acid monomer that can be suitably used include acrylic acid, methacrylic acid, 4-(meth)acryloxyethyltrimellitic acid, 11-(meth)acryloyloxy-1,1-undecane dicarboxylic acid, 1,4-di(meth)acryloyloxypyromellitic acid, 2-(meth)acryloyloxyethylmaleic acid, 2-(meth)acryloyloxyethylphthalic acid, and 2-(meth)acryloyloxyethylhexahydrophthalic acid as those having a carboxyl group as an acidic group; 2-methacrylamide-2-methylpropanesulfonic acid, 2-acrylamide-2-methylpropanesulfonic acid, p-vinylbenzenesulfonic acid, and vinylsulfonic acid as those having an acidic group; and 2-(meth)acryloyloxyethyldihydrogenphosphate, bis[2-(meth)acryloyloxyethyl]hydrogenphosphate, 2-(meth)acryloyloxyethylphenylhydrogenphosphate, 6-(meth)acryloyloxyhexyldihydrogenphosphate, 6-(meth)acryloyloxyhexylphenylhydrogenphosphate, 10-(meth)acryloyloxydecyldihydrogenphosphate, 1,3-di(meth)acryloylpropane-2-dihydrogenphosphate, 1,3-di(meth)acryloylpropane-2-phenylhydrogenphosphate, and bis[5-{2-(meth)acryloyloxyethoxycarbonyl}heptyl]hydrogenphosphate as those having a dihydrogen phosphate monoester group or a hydrogen phosphate diester group as an acidic group. These may be used alone or two or more of them may be combined.

Among these acid monomers, an acid monomer having a dihydrogen phosphate monoester group or a hydrogen phosphate diester group is favorably used, and an acid monomer represented by the following formula (however, R in the following formula represents a hydrogen atom or a methyl group) is particularly favorably used because the effect is particularly high.

[Chem. 5]

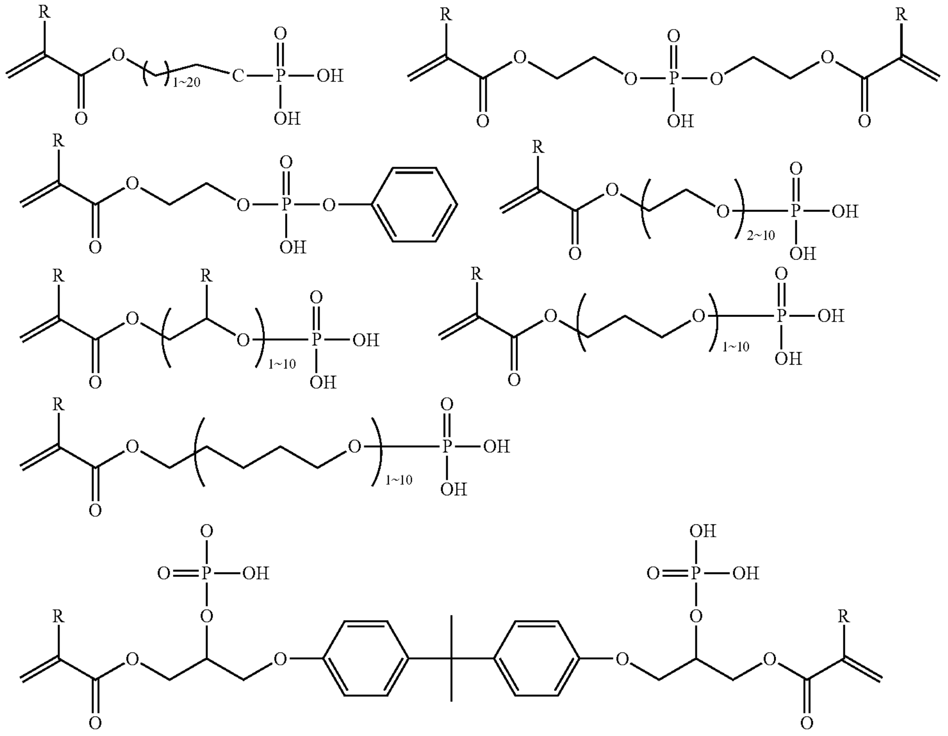

Note that as described above, the dental adhesive composition according to the present invention is characterized in that it exhibits high preservation stability and high adhesiveness when used as a one-liquid type dental adhesive material even in the case where an acid monomer of a system other than the "system in which a phosphonic acid group-containing polymerizable monomer and a multivalent carboxylic acid group-containing polymerizable monomer are combined" as an acid monomer. Therefore, from the viewpoint that the effect of the present invention is remarkable, an acid monomer "excluding one in which a phosphonic acid group-containing polymerizable monomer and a multivalent carboxylic acid group-containing polymerizable monomer are combined" is favorably used as an acid monomer.

The content of the (c1) component (acid monomer) in the dental composition according to the present invention is favorably 2 to 50 mass parts, and more favorably 5 to 30 mass parts when the total amount of the polymerizable monomer that is the (C) component is 100 mass parts, from the viewpoint of the adhesiveness and the preservation stability.

<Polymerizable Monomer (c2) Having No Acidic Group; (c2) Component>

The dental composition according to the present invention favorably further includes the polymerizable monomer (c2) having no acidic group other than the acid monomer (referred to also as the "non-acid monomer") from the viewpoint of adhesiveness. As the non-acid monomer that is the (c2) component, a compound that has no acidic group and has at least one polymerizable unsaturated group can be used without particular limitation. Examples of the non-acid monomer that can be suitably used include a monofunctional polymerizable monomer such as methyl(meth)acrylate, ethyl(meth)acrylate, butyl(meth)acrylate, glycidyl(meth)acrylate, 2-cyanomethyl(meth)acrylate, benzylmethacrylate, polyethylene glycol mono(meth)acrylate, allyl(meth)acrylate, 2-hydroxyethyl(meth)acrylate, 3-hydroxypropyl(meth) acrylate, and glyceryl mono(meth)acrylate; a polyfunctional polymerizable monomer such as ethylene glycol di(meth) acrylate, diethylene glycol di(meth)acrylate, triethylene glycol di(meth)acrylate, nonaethylene glycol di(meth)acrylate, propylene glycol di(meth)acrylate, dipropylene glycol di(meth)acrylate, 2,2'-bis[4-(meth)acryloyloxyethoxyphenyl]propane, 2,2'-bis[4-(meth)acryloyloxyethoxyethoxyphenyl]propane, 2,2'-bis[4-(meth)acryloyloxyethoxyethoxyethoxyethoxyethoxyphenyl]propane, 2,2'-bis{4-[2-hydroxy-3-(meth)acryloyloxypropoxy]phenyl}propane, 1,4-butanediol di(meth)acrylate, 1,6-hexanediol di(meth) acrylate, 1,9-nonanediol di(meth)acrylate, trimethylolpropane tri(meth)acrylate, neopentyl glycol di(meth)acrylate, 1,6-bis(methacrylethyloxycarbonylamino)-2,2,4-trimethylhexane, 1,6-bis(methacrylethyloxycarbonylamino)-2,4,4-trimethylhexane, urethane(meth)acrylate, epoxy(meth)acrylate, trimethylolpropane trimethacrylate, and pentaerythritol tetramethacrylate; a fumaric acid ester compound such as monomethyl fumarate, diethyl fumarate, and diphenyl fumarate; a styrene/α-methylstyrene derivative such as styrene, divinylbenzene, α-methylstyrene, and an α-methylstyrene dimer; and an allyl compound such as diallylphthalate, diallylterephthalate, diallylcarbonate, and allyldiglycolcarbonate. These may be used alone or two or more of them may be combined.

<Water (D); (D) Component>

The dental composition according to the present invention is capable of promoting the decalcification action by the acidic group-containing polymerizable monomer (c1) by including the water (D). Distilled water or ion exchanged water is favorable as the water to be used for preparing the dental composition according to the present invention in order to inhibit the introduction of impurities that adversely affect the adhesiveness. The content of the (D) component in the dental composition according to the present invention is favorably 2 to 20 mass parts, and more favorably 5 to 15 mass parts when the total amount of the polymerizable monomer (C) is 100 mass parts from the viewpoint of the compatibility with other components, the adhesiveness, and the preservation stability.

<Organic Solvent (E); (E) Component>

As the organic solvent (E), alcohols, ketones, ethers, an aromatic solvent, a hydrocarbon solvent, a chlorine solvent, a fluorine solvent, and the like can be used. However, from the viewpoint of low harmfulness, adhesiveness, and the like, a water-soluble organic solvent is favorably used. Examples of the water-soluble organic solvent that can be suitably used include acetone, ethanol, and isopropyl alcohol. Two or more kinds of (E) components may be combined and used as necessary.

The formulation amount of the (E) component is favorably 10 to 200 mass parts when the total amount of the polymerizable monomer (C) is 100 mass parts, from the viewpoints of viscosity suitable for coating, time and effort of drying by air blow or the like, and prevention of the mechanical strength of the adhesive material layer from decreasing due to residual in the adhesive material after air blow.

<Other Components>

The dental composition according to the present invention favorably includes a polymerization initiator from the viewpoint of the adhesiveness to a tooth substance. Further, the dental composition may contain a component such as a silane coupling agent other than the (A) component, a polymerization inhibitor, a polymerization accelerator, a pigment, a polymer, a filler, an antifungal agent, and an antibacterial agent to the extent that the effect of the present invention is not impaired. However, in the case where an inorganic filler having a silanol group on the surface thereof is formulated as a filler, the (A) component reacts therewith and the effect of the present invention is impaired. Therefore, it is favorable that the dental composition according to the present invention does not include an inorganic filler having a silanol group on the surface thereof.

Hereinafter, a polymerization initiator that is favorably formulated in the dental composition according to the present invention will be described in detail.

<Polymerization Initiator (F); (F) Component>

As the polymerization initiator (F), a photoinitiator or a chemical polymerization initiator used as a polymerization initiator in the existing dental adhesive composition can be used without particular limitation.

As a photoinitiator, a photosensitizer that generates radicals by light irradiation, specifically, a benzophenone compound, a thioxanthone compound, acylphosphine oxides, coumarins, and a halomethyl group substituted-s-triazine derivative, which are photosensitizers for ultraviolet rays, and α-diketones, which are photosensitizers for visible light, can be used. These photosensitizers (photoinitiators) can be used alone or two or more of them can be combined and used. A photopolymerization accelerator such as tertiary amines can also be combined therewith and used. From the viewpoint that it does not require ultraviolet rays that are harmful to a human body, as the photosensitizer, α-diketones, particularly, camphorquinone is favorably used and a combination of camphorquinone and a photopolymerization accelerator including amines in which an aromatic group such as p-dimethylaminobenzoic acid ethylester is directly substituted with a nitrogen atom is more favorably used.

As a chemical polymerization initiator, combinations of organic peroxides and amines; combinations of organic peroxides, amines, and sulfinates; combinations of acidic compounds and aryl borate compounds; combinations of 4th period transition metal compounds and organic peroxides; combinations of organic peroxides and thiourea derivatives; barbituric acid; alkyl borane, and the like can be used.

<Packaging Form>

The dental adhesive composition according to the present invention does not necessarily need to be used as a one-liquid type composition, and it goes without saying that the dental adhesive composition can be used as a separate package type composition divided into a plurality of packages depending on the purpose. From the viewpoint that weighing and mixing operations can be omitted, the dental adhesive composition is favorably used as a so-called one-liquid type composition contained in a single container. In the case of a dental adhesive material package in which the dental adhesive composition according to the present invention is contained in a single container, as the container, a container in which at least the inner surface thereof is formed of a resin is favorably used in order that no silanol group is present on the surface of the container, which can come into contact with an adhesive composition, and a container having a light-shielding property is favorably used from the viewpoint of preservation stability. In this case, as the (F) polymerization initiator, a polymerization initiator other than the chemical polymerization initiator is favorably used, and a photoinitiator is particularly favorably used.

Note that in the case of using a chemical polymerization initiator as the polymerization initiator (F), since the polymerization reaction is started when all the components (all of the reaction components) forming the chemical polymerization initiator coexist, it is necessary to separately package the reaction component described above during the preservation (storage). For this reason, it is necessary to preserve at least one of the reaction components separately from the dental composition according to the present invention and mix them at the time of use, thereby providing a multi-agent type one. Alternatively, in the case of providing a one-liquid type one, it is necessary to formulate some components of the reaction components in the dental composition according to the present invention and cause the remaining components to be supplied from an adherend or a pretreatment agent.

<Favorable Application of Dental Adhesive Composition (Adherend)>

The dental adhesive composition according to the present invention can be applied to various adherends. Specifically, the dental adhesive composition can be used for adhesion to various dental materials such as ceramics such as zirconia ceramics and silica ceramics (porcelain, etc.), a tooth substance (dentil, enamel), a base metal containing iron, nickel, chromium, cobalt, tin, aluminum, copper, titanium, or the like as the main component, a precious metal containing gold, platinum, palladium, silver, or the like as the main component, and a hardened resin (indirect composite resin teeth, hybrid resin, CAD/CAM resin block) containing a filler such as silica particles or silica-zirconia particles dispersed.

Among such applications for adhesion to an adherend, particularly, adhesiveness to ceramics having an adhesive surface formed of an inorganic substance having a silanol group on the surface thereof and a hardened resin containing silica particles is excellent. For this reason, the dental adhesive composition according to the present invention can be suitably used as a ceramic primer and a multipurpose adhesive material. Further, it is a favorable form in which such an adherend having an adhesive surface formed of an inorganic substance having a silanol group on the surface thereof and a curable composition containing a polymerizable monomer such as a dental bonding material or the cured body thereof are adhered to each other respectively as a first adherend and a second adherend by the dental adhesive composition according to the present invention.

Note that in the case where a chemical polymerization initiator is used as the polymerization initiator (F), some components of the reaction components are formulated in the dental composition according to the present invention, and the remaining components are caused to be supplied from an adherend, a pretreatment agent, or the like, as described above, a dental bonding material, a composite resin, a compomer, a resin core, a resin cement, a resin reinforced glass ionomer cement, a resin for denture base, and the like are suitably used as an adherend containing the remaining components.

EXAMPLE

Although the present invention will be specifically described below by way of Examples and Comparative Examples, the present invention is not limited by these.

1. First, substances, abbreviations thereof, and the like used in dental adhesive compositions according to Examples and Comparative Examples will be described below.

[Silane Coupling Agent (SCA)]

<(A) Hydrolysis-Resistant Silane Coupling Agent (Hydrolysis-Resistant SCA)>

TAPM: 3-(triallylsilyl)propylmethacrylate

TMPM: 3-(trimethallylsilyl)propylmethacrylate

DAMM: diallylsilylmethylmethacrylate

ADMPM: 3-(allyldimethylsilyl)propylmethacrylate.

<Silane Coupling Agent Other than (A) Component (Hydrolysable SCA)>

MPS: γ-methacryloxypropyltrimethoxysilane.

[(B) Fluoride Salt] •NaF: Sodium Fluoride

KF: potassium fluoride

CsF: cesium fluoride

TBAF: tetra-n-butylammonium fluoride trihydrate

TEAF: tetraethylammonium fluoride.

[(C) Polymerizable Monomer] <(c1) Acid Monomer>

MDP: 10-methacryloxydecyl dihydrogen phosphate (phosphoric acid group-containing polymerizable monomer)

AET: 4-acryloyloxyethyltrimellitic acid (carboxylic acid group-containing polymerizable monomer)

MHPA: 6-methacryloyloxyhexyl phosphonoacetate (phosphonic acid group-containing polymerizable monomer)

<(c2) Non-Acid Monomer>

HEMA: 2-hydroxyethylmethacrylate

Bis-GMA: bisphenol A di(2-hydroxypropoxy)dimethacrylate

UDMA: di(methacryloyloxy)-2,2,4-trimethylhexamethylene diurethane.

[(E) Organic Solvent] •EtOH: Ethanol

IPA: isopropanol

[(F) Polymerization Initiator] •CQ: camphorquinone

DMBE: p-dimethylaminobenzoic acid ethylester.

[Polymerization Inhibitor] •BHT: dibutylhydroxytoluene.

2. Next, a method of evaluating the dental adhesive materials prepared in the Examples and Comparative Examples will be described.

By performing an initial adhesiveness test and an adhesive durability test on respective systems of (1) a tooth substance/composite resin system (tooth substance/CR system) when a tooth substance and a composite resin are adhered to each other and (2) a porcelain material/resin cement system (P material/R cement system) when a porcelain material and a resin cement are adhered to each other by using the respective dental adhesive materials, the adhesiveness of the dental adhesive material was evaluated by the adhesive strength at that time.

Further, in order to examine the preservation stability, the evaluation described above was performed for the case where the composition immediately after preparation was used as an adhesive and the case where the composition after preservation at the temperature of 50° C. for two weeks after preparation was used as an adhesive. The evaluation method will be described below in detail.

[Preparation of Evaluation Sample (Sample)]

<Preparation of Sample for Measuring Adhesive Strength Between Tooth Substance-Composite Resin (Tooth Substance/CR System Adhesive Strength)>

Anterior teeth of a bovine, which had been removed within 24 hours after slaughter, were polished with water-resistant abrasive paper P600 under water injection to prepare adherends having an enamel plane cut out so as to be parallel to the lip surface and flat.

Next, a double-sided tape with a hole having a diameter of 3 mm was attached to the polished surface of adherends. Subsequently, each of the dental adhesive materials prepared in the Examples and Comparative Examples were applied to the adhesive surface exposed from the hole of the double-sided tape, of the polished surface, and air blown for 5 seconds to dry.

A paraffin wax having a thickness of 0.5 mm with a hole of a diameter of 8 mm was applied to the adhesive surface to which the dental adhesive material had been applied such that the hole of the paraffin wax and the hole of the double-sided tape were concentric to prepare a simulated cavity. This simulated cavity was filled with a dental composite resin (Estelite Σ Quick manufactured by Tokuyama Dental Corporation) and lightly pressed with a polyester film, and then, photocuring was performed by light irradiation for 10 seconds using a visible light irradiator (Elipar manufactured by 3MESPE). After that, a round bar formed of SUS304 (diameter of 8 mm and height of 18 mm) polished in advance was adhered with a resin cement (Bistite II manufactured by Tokuyama Dental Corporation) to prepare an evaluation sample (sample). Note that the used composite resin is a photopolymerizable composition containing camphorquinone and an amine compound.

<Preparation of Sample for Measuring Adhesive Strength Between Porcelain Material-Composite Resin (P Material/R Cement System Adhesive Strength)>

"NORITAKE SUPER PORCELAIN AAA" (manufactured by KURARAY NORITAKE DENTAL INC., length of 15 mm×width of 15 mm×thickness of 3 mm) that is dental ceramics (so-called porcelain) formed of silica crystallized glass was used as an adherend, and one side of the adherend was polished with water-resistant abrasive paper #800. After that, a double-sided tape with a hole of a diameter of 3 mm was attached to the polished surface of the adherend. Subsequently, each of the dental compositions according to the Examples and Comparative Examples was applied with a microbrush to the adhesive surface exposed from the hole of the double-sided tape, of the polished surface, and the dental composition applied to the adhesive surface was air blown for 5 seconds to dry. After that, a round bar formed of SUS304 (diameter of 8 mm and height of 18 mm) polished in advance was adhered with a resin cement (RelyX Ultimate Adhesive Resin Cement manufactured by 3MESPE) to prepare an evaluation sample (sample). Note that the used resin cement (RelyX Ultimate Adhesive Resin Cement manufactured by 3MESPE) is a chemically polymerizable composition.

[Initial Adhesive Strength Test]

The samples prepared as described above were divided into two test groups for each of the Examples or Comparative Examples, the respective samples were immersed in water at 37° C. for 24 hours for one test group, and then, the tensile adhesive strength (initial adhesive strength) was measured at a crosshead speed of 2 mm/min using a universal testing machine (autograph manufactured by Shimadzu Corporation). The measurement was performed within approximately one day from pulling the sample for measuring the adhesive strength out of the water. For each of the Examples and Comparative Examples, measurement values of four samples were averaged and used as the measurement results.

[Adhesive Durability Test]

For the other test group, samples for measuring adhesive durability were obtained by performing 3000 cycles of thermal cycles in which each of the samples was alternately immersed in constant temperature water baths of 5° C. and 55° C. for one minute, and the tensile adhesive strength (adhesive strength after the durability test) was measured in the same manner as that described above.

EXAMPLES AND COMPARATIVE EXAMPLES

Example 1

(1) Preparation of dental adhesive composition: 1.0 g of TAPM, 0.15 g of TBAF, 0.5 g of MDP, 1.0 g of purified water, 1.5 g of EtOH, 6.5 g of Bis-GMA, 3.0 g of HEMA, 0.01 g of BHT, 0.2 g of CQ, and 0.1 g of DMBE were mixed to obtained a dental composition.

(2) Evaluation of adhesiveness: The evaluation of adhesiveness described above was performed using the dental adhesive composition obtained in (1) as an adhesive material. The results of using the composition immediately after the preparation show high adhesive strength to a tooth substance, i.e., 18.8 MPa at the initial state and 16.4 MPa after the durability test. The adhesive strength to porcelain was also high, i.e., 25.7 MPa at the initial stage and 23.1 MPa after the durability test. Further, in the case of using the composition preserved at 50° C. for 2 weeks, the adhesive strength to a tooth substance was 17.3 MPa at the initial stage and 15.2 MPa after the durability test. The adhesive strength to porcelain was 23.9 MPa at the initial stage and 21.5 MPa after the durability test. Since favorable adhesive strength was shown even after preservation at 50° C. for 2 weeks, it can be said that the dental composition according to the present invention has excellent preservation stability.

Examples 2 to 31

Adhesive compositions were prepared in the same manner as that in the Example 1 except that the amount ratio of each component was changed as shown in Table 1, and the obtained compositions were used as adhesive materials to perform evaluation of adhesiveness and evaluation. The evaluation results are shown in Table 2, and high adhesive strength is shown both at the initial stage and after preservation in all Examples.

TABLE 1

| Example No. | (A) component: Hydrolysis-resistant SCA | (B) component: Fluoride salt | (C) component: Polymerizable monomer (c1) Acid monomer | (c2) Non-acid monomer | (D) component: Water | (E) component: Organic solvent | (B)/(A) mol ratio |
|---|---|---|---|---|---|---|---|
| 1 | TAPM(10) | TBAF(1.5) | MDP(5) | Bis-GMA(55) HEMA(40) | 10 | EtOH(15) | 0.2 |
| 2 | TAPM(0.3) | TBAF(1.5) | MDP(5) | Bis-GMA(55) HEMA(40) | 10 | EtOH(15) | 5.3 |
| 3 | TAPM(22) | TBAF(1.5) | MDP(5) | Bis-GMA(55) HEMA(40) | 10 | EtOH(15) | 0.1 |
| 4 | TAPM(10) | TBAF(5) | MDP(5) | Bis-GMA(55) HEMA(40) | 10 | EtOH(15) | 0.5 |
| 5 | TAPM(10) | TBAF(0.1) | MDP(5) | Bis-GMA(55) HEMA(40) | 10 | EtOH(15) | 0.01 |
| 6 | TAPM(10) | TBAF(1.5) | MDP(55) | Bis-GMA(25) HEMA(20) | 10 | EtOH(15) | 0.2 |

TABLE 1-continued

| Example No. | (A) component: Hydrolysis-resistant SCA | (B) component: Fluoride salt | (C) component: Polymerizable monomer (c1) Acid monomer | (c2) Non-acid monomer | (D) component: Water | (E) component: Organic solvent | (B)/(A) mol ratio |
|---|---|---|---|---|---|---|---|
| 7 | TAPM(10) | TBAF(1.5) | MDP(35) | Bis-GMA(35) HEMA(30) | 10 | EtOH(15) | 0.2 |
| 8 | TAPM(10) | TBAF(1.5) | MDP(2) | Bis-GMA(58) HEMA(40) | 10 | EtOH(15) | 0.2 |
| 9 | TAPM(10) | TBAF(1.5) | MDP(1) | Bis-GMA(59) HEMA(40) | 10 | EtOH(15) | 0.2 |
| 10 | TAPM(10) | TBAF(1.5) | MDP(3.5) AET(1.5) | Bis-GMA(55) HEMA(40) | 10 | EtOH(15) | 0.2 |
| 11 | TAPM(10) | TBAF(1.5) | MDP(4.5) AET(0.5) | Bis-GMA(55) HEMA(40) | 10 | EtOH(15) | 0.2 |
| 12 | TAPM(10) | TBAF(1.5) | MDP(3.5) MHPA(1.5) | Bis-GMA(55) HEMA(40) | 10 | EtOH(15) | 0.2 |
| 13 | TAPM(10) | TBAF(1.5) | MDP(5) | Bis-GMA(55) HEMA(40) | 22 | EtOH(15) | 0.2 |
| 14 | TAPM(10) | TBAF(1.5) | MDP(5) | Bis-GMA(55) HEMA(40) | 17 | EtOH(15) | 0.2 |
| 15 | TAPM(10) | TBAF(1.5) | MDP(5) | Bis-GMA(55) HEMA(40) | 3 | EtOH(15) | 0.2 |
| 16 | TAPM(10) | TBAF(1.5) | MDP(5) | Bis-GMA(55) HEMA(40) | 1 | EtOH(15) | 0.2 |
| 17 | TAPM(10) | NaF(0.2) | MDP(5) | Bis-GMA(55) HEMA(40) | 10 | EtOH(15) | 0.1 |
| 18 | TAPM(10) | KF(0.27) | MDP(5) | Bis-GMA(55) HEMA(40) | 10 | EtOH(15) | 0.1 |
| 19 | TAPM(10) | CsF(0.72) | MDP(5) | Bis-GMA(55) HEMA(40) | 10 | EtOH(15) | 0.1 |
| 20 | TAPM(10) | TEAF(0.7) | MDP(5) | Bis-GMA(55) HEMA(40) | 10 | EtOH(15) | 0.1 |
| 21 | TAPM(10) | TBAF(1.5) | MDP(5) | UDMA(55) HEMA(40) | 10 | EtOH(15) | 0.2 |
| 22 | TMPM(10) | TBAF(1.5) | MDP(5) | Bis-GMA(55) HEMA(40) | 10 | EtOH(15) | 0.2 |
| 23 | DAMM(10) | TBAF(1.5) | MDP(5) | Bis-GMA(55) HEMA(40) | 10 | EtOH(15) | 0.14 |
| 24 | ADMPM(10) | TBAF(1.5) | MDP(5) | Bis-GMA(55) HEMA(40) | 10 | EtOH(15) | 0.14 |
| 25 | TAPM(10) | TBAF(1.5) | MDP(5) | Bis-GMA(55) HEMA(40) | 10 | EtOH(15) | 0.2 |
| 26 | TAPM(10) | TBAF(1.5) | MDP(5) | Bis-GMA(55) HEMA(40) | 10 | Acetone(15) | 0.2 |
| 27 | TAPM(10) | TBAF(1.5) | MDP(5) | Bis-GMA(55) HEMA(40) | 10 | IPA(15) | 0.2 |
| 28 | TAPM(10) | TBAF(1.5) | MDP(5) | Bis-GMA(55) HEMA(40) | 10 | IPA(210) | 0.2 |
| 29 | TAPM(10) | TBAF(1.5) | MDP(5) | Bis-GMA(55) HEMA(40) | 10 | IPA(5) | 0.2 |
| 30 | TAPM(10) | TBAF(0.05) | MDP(5) | Bis-GMA(55) HEMA(40) | 10 | EtOH(15) | 0.005 |
| 31 | TAPM(1) | TBAF(10) | MDP(5) | Bis-GMA(55) HEMA(40) | 10 | EtOH(15) | 10.6 |

※ In all Examples other than Example 24, CQ (2) and DMBE (1) are formulated as (F) polymerization initiator. (Example 24: No (F) component)
In all Examples, polymerization inhibitor BHT (0.1) is formulated.

TABLE 2

| Example No. | Immediately after preparation: Tooth substance/CR system: Initial adhesive strength (MPa) | Adhesive strength after durability test (MPa) | P material/R cement system: Initial adhesive strength (MPa) | Adhesive strength after durability test (MPa) | After preservation at 50° C. for 2 weeks: Tooth substance/CR system: Initial adhesive strength (MPa) | Adhesive strength after durability test (MPa) | P material/R cement system: Initial adhesive strength (MPa) | Adhesive strength after durability test (MPa) |
|---|---|---|---|---|---|---|---|---|
| 1 | 18.8 | 16.4 | 25.7 | 23.1 | 17.3 | 15.2 | 23.9 | 21.5 |
| 2 | 18.2 | 16.9 | 28.2 | 16.2 | 17.5 | 16.1 | 16.6 | 14.7 |
| 3 | 14.6 | 12.5 | 25.9 | 23.4 | 13.8 | 11.1 | 24.0 | 21.9 |
| 4 | 17.5 | 15.3 | 17.4 | 15.7 | 15.9 | 13.4 | 16.4 | 13.0 |
| 5 | 19.7 | 16.1 | 16.8 | 15.3 | 17.2 | 15.6 | 15.1 | 13.7 |
| 6 | 17.3 | 12.7 | 24.6 | 18.6 | 15.7 | 11.9 | 22.7 | 16.2 |
| 7 | 18.1 | 14.6 | 23.7 | 22.0 | 16.5 | 13.5 | 21.5 | 20.1 |
| 8 | 15.6 | 13.8 | 25.1 | 23.3 | 14.1 | 13.2 | 23.8 | 21.4 |
| 9 | 13.4 | 12.4 | 22.9 | 21.2 | 11.6 | 10.3 | 22.2 | 20.6 |
| 10 | 15.5 | 12.3 | 24.5 | 22.8 | 15.2 | 11.0 | 22.8 | 21.1 |
| 11 | 16.8 | 14.7 | 23.8 | 21.4 | 15.9 | 13.5 | 21.8 | 20.4 |
| 12 | 16.8 | 13.7 | 23.2 | 21.4 | 15.3 | 13.4 | 22.4 | 20.9 |
| 13 | 13.7 | 12.9 | 23.3 | 21.5 | 11.5 | 10.7 | 21.4 | 20.8 |
| 14 | 16.1 | 14.6 | 25.1 | 23.7 | 14.8 | 13.8 | 23.2 | 21.9 |
| 15 | 16.5 | 14.8 | 24.0 | 22.3 | 14.4 | 13.6 | 22.9 | 21.0 |
| 16 | 14.0 | 12.5 | 23.1 | 21.9 | 12.3 | 11.5 | 21.1 | 20.7 |
| 17 | 18.4 | 16.1 | 16.5 | 15.2 | 16.5 | 15.0 | 14.6 | 13.3 |
| 18 | 18.0 | 17.7 | 16.2 | 15.0 | 16.7 | 15.1 | 14.4 | 13.7 |
| 19 | 18.1 | 17.8 | 16.0 | 15.3 | 16.9 | 15.5 | 14.5 | 13.8 |
| 20 | 18.7 | 17.5 | 25.1 | 22.9 | 17.1 | 16.0 | 23.4 | 21.3 |
| 21 | 17.4 | 16.6 | 23.5 | 21.8 | 16.0 | 15.3 | 21.0 | 20.2 |
| 22 | 18.3 | 16.9 | 17.7 | 15.7 | 16.8 | 15.6 | 16.1 | 14.8 |
| 23 | 17.6 | 16.3 | 23.9 | 21.2 | 16.2 | 15.4 | 22.3 | 20.6 |
| 24 | 17.9 | 16.4 | 17.4 | 15.0 | 16.5 | 15.4 | 16.8 | 14.4 |
| 25 | 14.2 | 13.5 | 25.5 | 23.6 | 13.5 | 13.0 | 23.2 | 21.7 |
| 26 | 18.0 | 16.7 | 23.8 | 22.1 | 16.7 | 15.2 | 22.9 | 20.5 |
| 27 | 17.8 | 16.5 | 23.5 | 21.9 | 16.6 | 15.7 | 21.6 | 20.0 |
| 28 | 15.9 | 12.2 | 22.7 | 21.4 | 14.4 | 11.3 | 21.1 | 20.3 |

TABLE 2-continued

| | Immediately after preparation | | | | After preservation at 50° C. for 2 weeks | | | |
|---|---|---|---|---|---|---|---|---|
| | Tooth substance/CR system | | P material/R cement system | | Tooth substance/CR system | | P material/R cement system | |
| Example No. | Initial adhesive strength (MPa) | Adhesive strength after durability test (MPa) | Initial adhesive strength (MPa) | Adhesive strength after durability test (MPa) | Initial adhesive strength (MPa) | Adhesive strength after durability test (MPa) | Initial adhesive strength (MPa) | Adhesive strength after durability test (MPa) |
| 29 | 15.5 | 12.0 | 24.3 | 22.7 | 14.1 | 10.9 | 22.7 | 21.1 |
| 30 | 17.7 | 16.4 | 18.1 | 11.9 | 16.0 | 15.2 | 16.5 | 10.5 |
| 31 | 17.4 | 16.5 | 17.9 | 12.0 | 15.9 | 15.0 | 15.1 | 10.2 |

Comparative Examples 1 to 8

Preparation of compositions and evaluation thereof were performed in the same manner as those in the Example 1 except that the amount ratio of each component was changed as shown in Table 3. The evaluation results are shown in Table 4.

In the case where a silane coupling agent was a hydrolysable silane coupling agent (Comparative Example 1), adhesive strength to porcelain after the durability test after preservation at 50° C. was low. This is because inactivation has occurred due to condensation of the silane coupling agent. In the case where no fluoride ion source was contained (Comparative Example 2 and Comparative Examples 6 to 8), the silane coupling agent was not activated and adhesive strength to porcelain was low both immediately after the preparation and after preservation at 50° C. In the case where no acidic group-containing polymerizable monomer was contained (Comparative Example 3), adhesive strength to a tooth substance was reduced because decalcification was insufficient and the amount of the adhesive component was small. In the case where no water was contained (Comparative Example 4), adhesive strength to a tooth substance was reduced because decalcification of the tooth substance was insufficient. In the case where no solvent is contained (Comparative Example 5), a uniform dental composition could not be prepared because water and the monomer component were incompatible.

TABLE 3

| | Silane coupling agent: SCA | | | | | | | |
|---|---|---|---|---|---|---|---|---|
| Comparative Example No. | (A) component Hydrolysis-resistant | Hydrolysis | (B) component: Fluoride salt | (C) component: Polymerizable monomer (c1) Acid monomer | (c2) Non-acid monomer | (D) component: Water | (E) component: Organic solvent | (B)/(A) mol ratio |
| 1 | — | MP3(10) | TBAF(1.5) | MDP(5) | Bis-GMA(55) HEMA(40) | 10 | EtOH(15) | 0.14 |
| 2 | TAPM(10) | — | — | MDP(5) | Bis-GMA(55) HEMA(40) | 10 | EtOH(15) | 0.0 |
| 3 | TAPM(10) | — | TBAF(1.5) | — | Bis-GMA(55) HEMA(40) | 10 | EtOH(15) | 0.2 |
| 4 | TAPM(10) | — | TBAF(1.5) | MDP(5) | Bis-GMA(55) HEMA(40) | — | EtOH(15) | 0.2 |
| 5 | TAPM(10) | — | TBAF(1.5) | MDP(5) | Bis-GMA(55) HEMA(40) | 10 | — | 0.2 |
| 6 | TAPM(10) | — | — | MDP(3.5) AET(1.5) | Bis-GMA(55) HEMA(40) | 10 | EtOH(15) | 0.0 |
| 7 | TAPM(10) | — | — | MDP(4.5) AET(0.5) | Bis-GMA(55) HEMA(40) | 10 | EtOH(15) | 0.0 |
| 8 | TAPM(10) | — | — | MDP(3.5) MHPA(1.5) | Bis-GMA(55) HEMA(40) | 10 | EtOH(15) | 0.0 |

In all Comparative Examples, CQ (2) and DMBE (1) are formulated as (F) polymerization initiator.

In all Comparative Examples, polymerization inhibitor BHT (0.1) is formulated.

TABLE 4

| | Immediately after preparation | | | | After preservation at 50° C. for 2 weeks | | | |
|---|---|---|---|---|---|---|---|---|
| | Tooth substance/CR system | | P material/R cement system | | Tooth substance/CR system | | P material/R cement system | |
| Comparative Example No. | Initial adhesive strength (MPa) | Adhesive strength after durability test (MPa) | Initial adhesive strength (MPa) | Adhesive strength after durability test (MPa) | Initial adhesive strength (MPa) | Adhesive strength after durability test (MPa) | Initial adhesive strength (MPa) | Adhesive strength after durability test (MPa) |
| 1 | 18.2 | 16.3 | 23.2 | 20.4 | 17.1 | 15.5 | 12.3 | 3.5 |
| 2 | 18.0 | 16.7 | 15.5 | 0.3 | 16.6 | 15.8 | 13.8 | 0.1 |
| 3 | 3.8 | 0.2 | 17.9 | 14.2 | 1.7 | 0.2 | 15.4 | 12.2 |
| 4 | 5.1 | 0.5 | 16.6 | 14.0 | 2.2 | 0.2 | 13.9 | 11.9 |
| 5 | Incompatible | | | | | | | |
| 6 | 17.9 | 16.4 | 15.8 | 0.2 | 16.7 | 15.5 | 13.9 | 0.1 |
| 7 | 18.3 | 16.5 | 15.6 | 0.3 | 2.2 | 0.2 | 13.7 | 0.2 |
| 8 | 18.0 | 0.5 | 15.3 | 0.2 | 2.2 | 0.2 | 13.4 | 0.1 |

The invention claimed is:

1. A dental adhesive composition, comprising:

a mixture that includes a silane coupling agent (A) that does not have a silyl ether structure and includes an organic silane compound (a1) in which four monovalent groups are bonded to one silicon atom, the four monovalent groups including (i) a monovalent group having a radical polymerizable group and (ii) a monovalent group that has an alkylene chain having 3 to 40 carbon atoms and has an unsaturated bond in a carbon atom at a B-position from the silicon atom, a fluoride salt (B), a polymerizable monomer (C) that contains an acidic group-containing polymerizable monomer (c1) and a polymerizable monomer (c2) having no acidic group, water (D), an organic solvent (E), and a polymerization initiator (F), wherein the acidic group-containing polymerizable monomer (c1) excludes a combination of a phosphonic acid group-containing polymerizable monomer and a multivalent carboxylic acid group-containing polymerizable monomer.

2. The dental adhesive composition according to claim 1, wherein the (a1) organic silane compound is represented by the following general formula (1)

[Chem. 1]

(1)

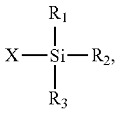

wherein in the general formula (1),

X represents a monovalent organic group having a monovalent organic group having a radical polymerizable group, $R_1$, $R_2$, and $R_3$ represent monovalent organic groups of the same kind or different kinds, and at least one of $R_1$, $R_2$, and $R_3$ represents a monovalent organic group represented by the following general formula (2)

[Chem. 2]

(2)

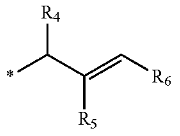

wherein in general formula (2),

* represents a position where the monovalent organic group is bonded to a silicon atom in the general formula (1), and $R_4$, $R_5$, and $R_6$ each represent a hydrogen atom; a phenyl group; an unsubstituted alkyl group having 1 to 20 carbon atoms; a substituted alkyl group having 1 to 20 carbon atoms in which 1 or a plurality of hydrogen atoms are substituted with at least one of an alkoxy group, a siloxy group, and an amino group; or a monovalent organic group having an —O— bond, a —C(═O)—O— bond, or an —NH— bond between a C—C bond of a main chain of the unsubstituted alkyl group or the substituted alkyl group having 2 to 20 carbon atoms.

3. The dental adhesive composition according to claim 1, wherein 0.01 to 10 mol of the fluoride salt (B) with respect to 1 mol of the organic silane compound (a1) is contained.

4. A dental adhesive material, comprising:

the dental adhesive composition according to claim 1.

5. The dental adhesive material according to claim 4, which is a dental adhesive material for adhering a first adherend that has an adhesive surface formed of an inorganic substance having a silanol group on a surface thereof and a second adherend that includes a curable composition containing a polymerizable monomer or a cured body thereof to each other.

6. A dental adhesive material package, comprising:

the dental adhesive composition according to claim 1 contained in a single container.

* * * * *